United States Patent
Mistretta et al.

(10) Patent No.: US 8,755,584 B2
(45) Date of Patent: Jun. 17, 2014

(54) SYSTEM AND METHOD FOR FILTRATION REDUCED EQUALIZED EXPOSURE COMPUTED TOMOGRAPHY

(75) Inventors: Charles A. Mistretta, Madison, WI (US); Charles M. Strother, Madison, WI (US)

(73) Assignees: Mistretta Medical, LLC, Madison, WI (US); CMS Medical, LLC, Madison, WI (US)

( * ) Notice: Subject to any disclaimer, the term of this patent is extended or adjusted under 35 U.S.C. 154(b) by 736 days.

(21) Appl. No.: 13/011,789

(22) Filed: Jan. 21, 2011

(65) Prior Publication Data
US 2011/0206259 A1 Aug. 25, 2011

Related U.S. Application Data

(60) Provisional application No. 61/297,770, filed on Jan. 24, 2010.

(51) Int. Cl.
| | |
|---|---|
| *G06K 9/00* | (2006.01) |
| *A61B 6/00* | (2006.01) |
| *A61B 6/03* | (2006.01) |
| *G21K 1/10* | (2006.01) |

(52) U.S. Cl.
CPC .............. *A61B 6/4035* (2013.01); *G21K 1/10* (2013.01); *A61B 6/032* (2013.01); *G21K 2207/00* (2013.01)
USPC .......................................... 382/131; 382/128

(58) Field of Classification Search
CPC ................... G06T 7/0012; G06T 2207/10116; G06T 2207/30004; G06T 7/0083; G06F 19/3418; G06F 19/322; G06F 7207/30072; G06F 19/321; G01N 15/1475; G09B 19/00; G09B 7/04; A61B 5/0002; A61B 6/4035; G21K 1/10; G21K 2207/00
USPC .............. 382/100, 128–134; 378/4, 8, 21–27, 378/101, 901; 600/407, 410–411, 425, 427, 600/435, 437; 606/1, 45, 130, 159; 128/920, 922
See application file for complete search history.

(56) References Cited

U.S. PATENT DOCUMENTS

| | | | |
|---|---|---|---|
| 4,497,062 A | 1/1985 | Mistretta et al. | |
| 5,565,684 A * | 10/1996 | Gullberg et al. | ......... 250/363.04 |
| 5,668,371 A | 9/1997 | Deasy et al. | |

(Continued)

FOREIGN PATENT DOCUMENTS

WO  WO-2011/022336  2/2011

OTHER PUBLICATIONS

U.S. Appl. No. 14/126,030, filed Jun. 14, 2012, Mistretta et al.

(Continued)

*Primary Examiner* — Hadi Akhavannik
*Assistant Examiner* — Mehdi Rashidian
(74) *Attorney, Agent, or Firm* — Foley & Lardner LLP

(57) ABSTRACT

A method is disclosed for producing a computed tomographic image of a subject, the method including: using a radiation source and detector, obtaining radiation transmission information relating to a region of interest in the subject; using the source and detector; obtaining a series of projection images of the region of interest. Each projection image is obtained by: directing an imaging beam of radiation from the source through the region of interest onto the detector along a respective direction; the detector having a detection area.

38 Claims, 14 Drawing Sheets

(56) References Cited

U.S. PATENT DOCUMENTS

| | | | |
|---|---|---|---|
| 6,480,565 B1* | 11/2002 | Ning | 378/37 |
| 7,444,011 B2* | 10/2008 | Pan et al. | 382/131 |
| 7,949,089 B2* | 5/2011 | Dafni et al. | 378/9 |
| 8,451,972 B2* | 5/2013 | Dafni | 378/8 |
| 2003/0073893 A1* | 4/2003 | Hsieh | 600/407 |
| 2003/0128801 A1* | 7/2003 | Eisenberg et al. | 378/19 |
| 2009/0175562 A1* | 7/2009 | Pan et al. | 382/312 |
| 2009/0257551 A1* | 10/2009 | Dafni et al. | 378/6 |
| 2010/0308228 A1* | 12/2010 | Vija et al. | 250/363.04 |
| 2011/0037761 A1 | 2/2011 | Mistretta et al. | |
| 2011/0038517 A1 | 2/2011 | Mistretta et al. | |
| 2011/0168774 A1* | 7/2011 | Magal | 235/375 |
| 2011/0170757 A1* | 7/2011 | Pan et al. | 382/131 |
| 2012/0114217 A1 | 5/2012 | Mistretta et al. | |
| 2012/0215090 A1* | 8/2012 | Pan et al. | 600/407 |
| 2013/0046176 A1 | 2/2013 | Mistretta et al. | |

OTHER PUBLICATIONS

U.S. Appl. No. 14/135,259, filed Dec. 19, 2013, Mistretta Medical, LLC et al.

U.S. Appl. No. 61/297,770, filed Jan. 24, 2010, Mistretta et al.

U.S. Appl. No. 61/297,771, filed Jan. 24, 2010, Mistretta et al.

U.S. Appl. No. 61/389,086, filed Oct. 1, 2010, Mistretta et al.

U.S. Appl. No. 61/497,392, filed Jun. 15, 2011, Mistretta et al.

Graham et al., Compensators for Dose and Scatter Management in Cone-Beam Computed Tomography, Medical Physics, 2007, pp. 2691-2703, vol. 34, 13 pages.

Graham et al., Intensity-Modulated Fluence Patterns for Task-Specific Imaging in Cone-Beam CT, SPIE Medical Imaging 2007: Physics of Medical Imaging, Proceedings of the SPIE, 2007, pp. 651003-1-651003-9, vol. 6510, 9 pages.

\* cited by examiner

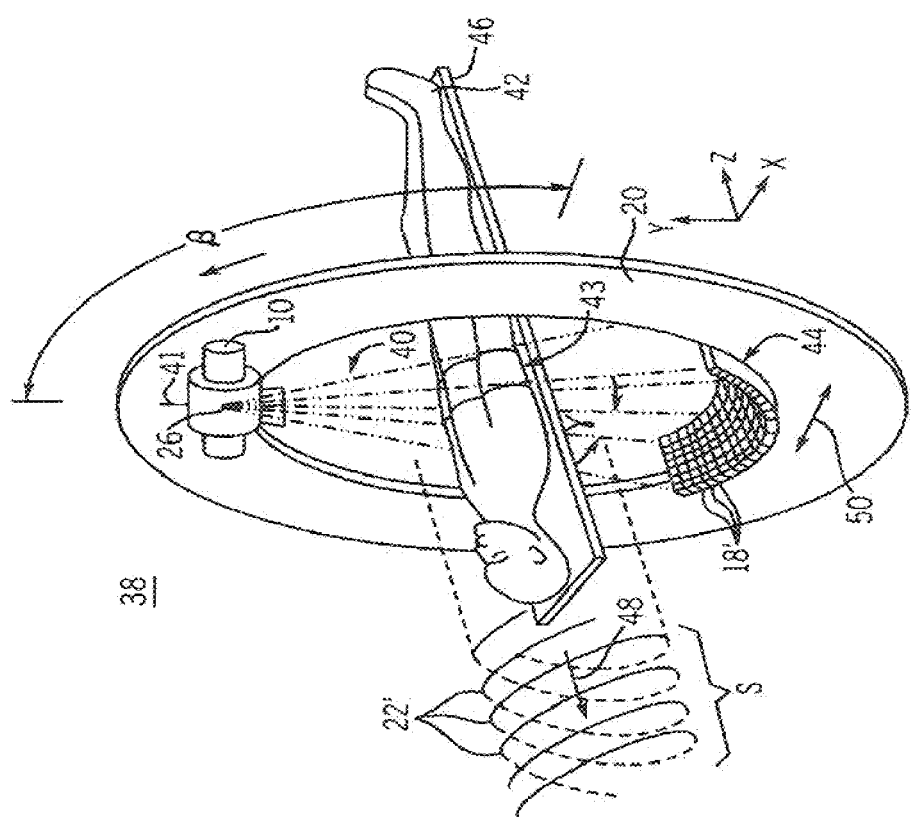

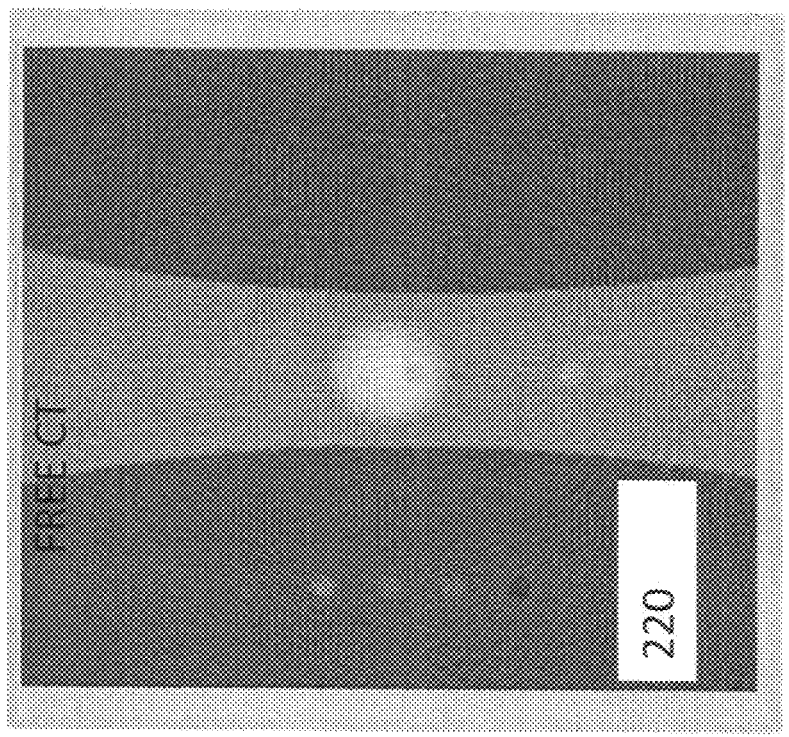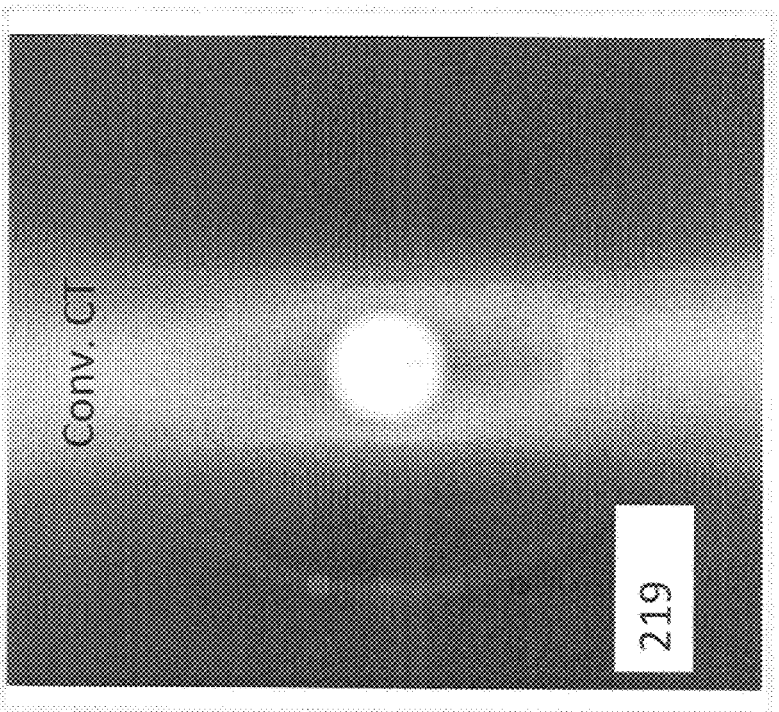
Fig. 7G

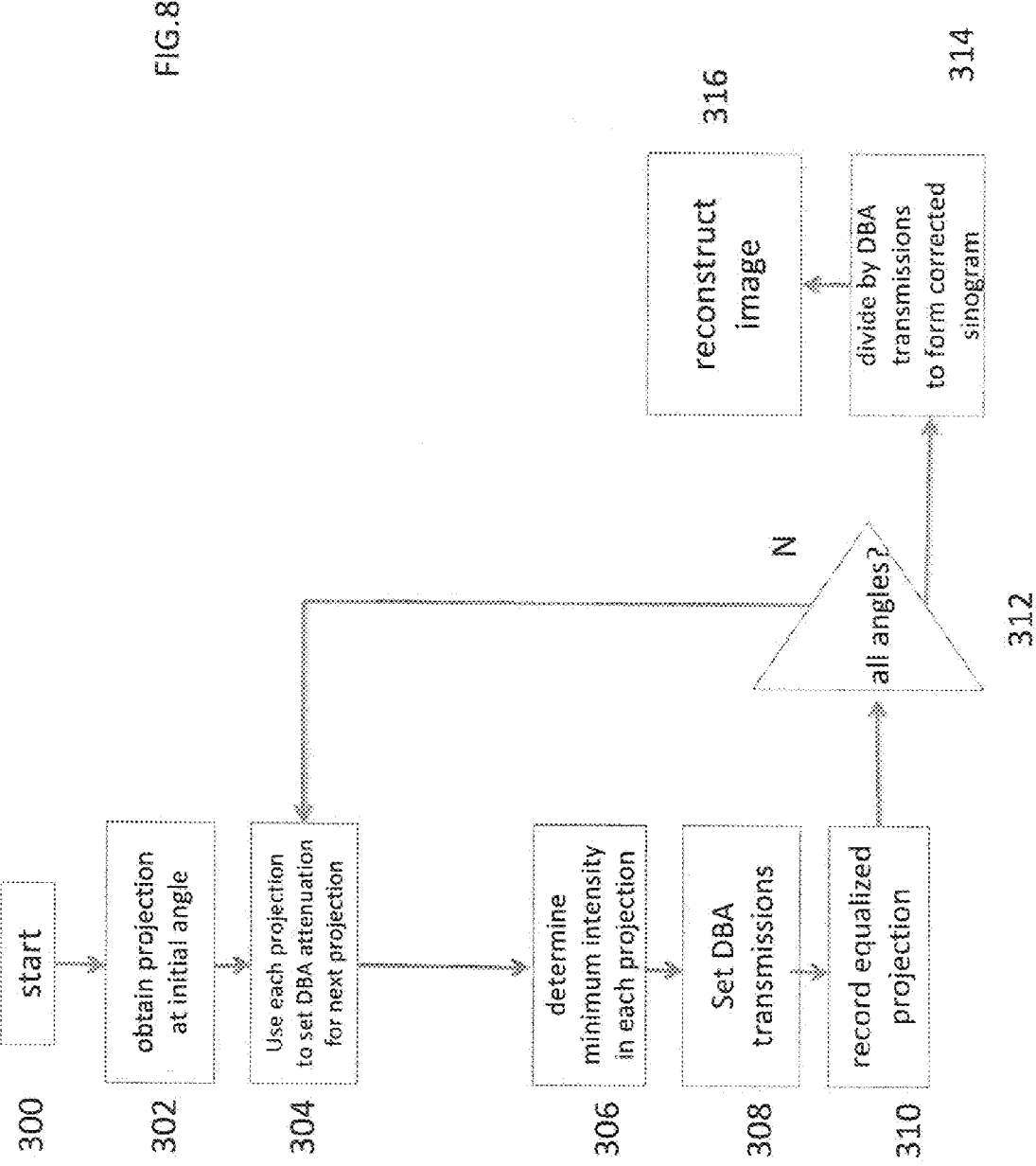

SYSTEM AND METHOD FOR FILTRATION REDUCED EQUALIZED EXPOSURE COMPUTED TOMOGRAPHY

CROSS REFERENCE TO RELATED APPLICATIONS

This application claims benefit of U.S. Provisional Patent Application No. 61/297,770 titled SYSTEM AND METHOD FOR FILTRATION REDUCED EQUALIZED EXPOSURE: COMPUTED TOMOGRAPHY filed Jan. 24, 2010, the entire contents of which are hereby incorporated by reference in their entirety herein.

FIELD

The present invention generally relates to a system and method for generating computed tomography (CT) images. More particularly, various embodiments of the present invention relate to generating CT images using anatomy-selective distribution of incident radiation.

BACKGROUND

X-Ray Computed Tomography (CT) was introduced in the late 1970s as a means for forming three dimensional images of human anatomy. Although its initial spatial resolution was inferior to that of film radiography, it brought a new level of contrast resolution that enabled radiologists to discern previously undetectable low contrast pathology. The apparatus configuration evolved through many generations and is often configured using a rotating X-ray source which is opposed by a detector array rotating in fixed relationship to the source. The x-ray source is often mounted on a C-arm system or conventional gantry. The detector arrays often consist of two dimensional arrays of discrete detectors in conventional CT or in the form of a large area cone beam flat panel detector in C-Arm CT.

Conventional CT is used for a wide range of diagnostic tasks and generally rather scatter free signal detection due to the smaller area of the detector arrays, although these areas are increasing in recent years. C-Arm CT is typically used for interventional procedures where it has been recently possible to obtain 3D Digital Subtraction Angiographic data reconstructions by performing a CT angiogram following the introduction of iodine contrast into the vascular system. CT angiography can also be implemented on conventional CT systems but due to the small detector area, the injected contrast bolus must be followed and the timing of the gantry or table advanced relative to the bolus traversal, which can pose timing problems that result images being obtained during suboptimal opacification.

In the 1980's the concept of spiral CT was introduced. In this mode, rather than obtaining one slice at a time, the table is advanced through the rotating gantry and the x-rays passed through the patient in a helical fashion. Using data interpolation, reconstruction of a series of CT images of sequential planes can be quickly obtained.

One of the limitations of conventional CT from its inception is the fact that a rather uniform distribution of X-rays is sent to all parts of the anatomy regardless of the anatomical thickness. Because of this, dose is more than necessary in thin regions and the X-ray beam parameters are generally chosen to guarantee penetration of the least transmissive regions.

DIGITAL BEAM ATTENUATOR, Mistretta et al. U.S. Pat. No. 4,497,062 (1985) describes a digitally controlled x-ray beam attenuation method and apparatus. A large area phosphor plate detector was used to digitally record a chest radiograph. The information from this radiograph was used to drive a dot matrix printer equipped with a cerium ribbon. The printer produced a Cerium mask that filtered the incident X-ray beam used for a subsequent chest radiography in which an optimal amount of radiation was sent to each point of the patient's chest. Smaller amounts of radiation were sent to the lungs than to the diaphragm and mediastinum. The result was increased detection of lung nodules in the typically underpenetrated regions.

Deasy et al. (U.S. Pat. No. 5,668,371) describes a multi-leaf collimator system for tailoring the depth of proton Bragg peaks in proton radiotherapy applications.

It would be advantageous to overcome the deficiencies described above, specifically those directed at correcting a major deficiency in C-Arm CT in which contrast resolution is inferior to that of conventional CT. For this reason it has been difficult to adequately visualize areas in the brain where bleeding has occurred using the C-Arm equipment typically available in the neuro-interventional suite. Patients typically must be also sent to conventional CT for visualization of subtle soil tissue images.

SUMMARY

The inventors have realized that techniques described in this application will reduce or eliminate the need for conventional CT, e.g., in these cases described above and permit, in some embodiments, all imaging and interventions to be performed using the C-Arm system. Accordingly, various embodiments of the present invention overcome the limitations of C-Arm CT and conventional CT to provide superior image quality and diagnostic value.

Various embodiments provide increased contrast resolution for C-Arm or conventional CT soft tissue scans due to scatter reduction and/or an improved of optimized distribution of the incident X-rays.

In one aspect, a method is disclosed for producing a computed tomographie image of a subject, the method including: using a radiation source and detector, obtaining radiation transmission information relating to a region of interest in the subject; using the source and detector; obtaining a series of projection images of the region of interest, where each projection image is obtained by: directing an imaging beam of radiation from the source through the region of interest onto the detector along a respective direction; the detector having a detection area; and detecting the transmission of the beam through the region of interest. The method includes collimating the detector by obscuring a portion of the detector area to block radiation scattered from the imaging beam; and while obtaining the series of projection images, filtering the imaging beam to provide a selected filtered beam intensity profile for each projection; where, for each projection image, the corresponding selected filtered beam intensity profile is determined based at least in part on the radiation transmission information.

In some embodiments, the series of projection images are obtained using a C-arm device with a movable subject table, the C-arm imaging device including the source and the detector. Some embodiments include employing the C-Arm imaging device to obtain the series of projection images by scanning the position of the source and detector relative to the subject using at least one of table motion or motion of a C-arm of the C-arm imaging device in a direction substantially parallel to an axis of rotation of the C-Arm of the C-arm imaging device. In some embodiments, the scan is a step and shoot scan. In some embodiments, the scan is a modified spiral scan.

In some embodiments, the selected beam intensity profile for each projection image in the series is determined using unfiltered transmission information indicative of a detected transmission a corresponding unfiltered beam directed from the source to the detector.

In some embodiments, the series of projection images is obtained at a first dosage level. Some embodiments include, prior to obtaining the series of projection images, conducting a pre-scan with an unfiltered radiation beam at a pre-scan dosage less than the first dosage level to determine the unfiltered transmission information.

In some embodiments, the filtration applied to the imaging beam for each image projection is determined at least in part based on the detected transmission values of a respective adjacent projection in the series.

In some embodiments, each projection in the series is obtained within about 0.1 seconds or less of the respective adjacent projection.

In some embodiments, each projection in the series is obtained within about 0.03 seconds or less of the respective adjacent projection.

Some embodiments include: generating a sinogram based on the series of projection images; and correcting the sinogram based on information indicative of filtration applied to the imaging beam for each projection. In some embodiments, correcting the sinogram includes dividing each point in the sinogram by a corresponding filter transmission value. Some embodiments include constructing an image of the region of interest based on the corrected sinogram.

Some embodiments include determining background level information indicative of a scattered radiation background level based on radiation detected at an obscured portion of the detector area; and correcting at least one image projection based on the background level information.

In some embodiments, the source and detector are components of a C-arm imaging device.

In some embodiments, the source and detector are components of a conventional computed tomography imaging device.

Some embodiments include: generating a time resolved series of images of the region of interest based at least in part on the series of projection images; generating a time independent three dimensional volume reconstruction of the region of interest; and generating a time resolved series of three dimensional volume reconstructions of the region based at least in part on the time resolved series of images and the time independent three dimensional volume reconstruction.

In another aspect, n apparatus for producing a computed tomographic image of a subject is disclosed, the apparatus including: a radiation source; a radiation detector having a detection area; and a processor in communication with the source and the detector configured to: obtain radiation transmission information relating to a region of interest in the subject; obtain a series of projection images of a region of interest, where each projection image is obtained by control the source to direct an imaging beam of radiation from a source through the region of interest onto a detector along a respective direction; and use the detector to detect the transmission of the beam through the region of interest. The apparatus includes a collimator configured to collimate the detector by obscuring a portion of the detector area to block radiation scattered from the imaging beam; and a dynamic beam attenuator in communication with the processor and configured to filter the imaging beam to provide a selected filtered beam intensity profile for each projection, where, for each projection image, the corresponding selected filtered beam intensity profile is determined based at least in part on the radiation transmission information.

Some embodiments include a C-arm imaging device with a movable subject table, the C-arm imaging device including the source and the detector in communication with the processor. In some embodiments, the processor is configured to control the C-Arm imaging device to obtain the series of projection images by scanning the position of the source and detector relative to the subject using at least one of table motion or motion of a C-arm of the C-arm imaging device in a direction substantially parallel to an axis of rotation of the C-Arm of the C-arm imaging device.

In some embodiments, the scan is a step and shoot scan or a modified spiral scan.

In some embodiments, the selected beam intensity profile for each projection image in the series is determined using unfiltered transmission information indicative of a detected transmission a corresponding unfiltered beam directed from the source to the detector.

In some embodiments, the series of projection images is obtained at a first dosage level; and where the processor is configured to control the source and detector to, prior to obtaining the series of projection images, conduct a pre-scan with an unfiltered radiation beam at a pre-scan dosage less than the first dosage level to determine the unfiltered transmission information. In some embodiments, the digital beam attenuator is configured to apply filtration to the imaging beam for each image projection at least in part based on the detected transmission values of an adjacent projection in the series.

In some embodiments, the processor is configured to: generate a sinogram based on the series of projection images; and correct the sinogram based on information indicative of filtration applied to the imaging beam for each projection. In some embodiments, the sinogram is corrected by dividing each point in the sinogram by a corresponding filter transmission value. In some embodiments, the processor is configured to construct an image of the region of interest based on the corrected sinogram.

In some embodiments, the processor is configured to: determine background level information indicative of a scattered radiation background level based on radiation detected at an obscured portion of the detector area; and correct at least one image projection based on the background level information.

Some embodiments include a C-arm imaging device including the source and detector.

Some embodiments include a conventional computed tomography imaging device including the source and detector.

In some embodiments, the processor is configured to: generate a time resolved series of images of the region of interest based at least in part on the series of projection images; generate a time independent three dimensional volume reconstruction of the region of interest; and generate a time resolved series of three dimensional volume reconstructions of the region based at least in part on the time resolved series of images and the time independent three dimensional volume reconstruction.

In some embodiments, the attenuator includes an array of filter elements controlled by the processor to provide selected filtered beam intensity profile.

In some embodiments, the process controls the thickness of each filter element to modulate the intensity of a corresponding portion of the imaging beam. In some embodiments, at least one filter element including a pair of opposing wedge shaped members which are actuated by processor to control the thickness of the element.

In another aspect, a method is disclosed of providing time dependent three dimensional imaging of a region of a patient including blood vessels in a perfusion bed, the method including: generating a time independent 3D volume reconstruction of the region based on a series of image projections of the region acquired over a wide range of projection angles; generating a series of time resolved image projections of the region, at least in part, using any of the methods for producing a computed tomographic image of a subject described above; and generating a time resolved series of limited sector 3D volume reconstructions of the region, where generating each limited sector 3D volume reconstruction in the series includes: selecting a respective limited sector set of image projections from the series of time resolved image projections, the limited sector set of image projections including of projections in a limited range of projection angles less than the wide range of projection angles; and generating the limited sector 3D volume reconstruction based on the respective limited sector set of projections and constrained by the time independent 3D volume reconstruction. In some embodiments, the projections are subtracted angiography projections. In some embodiments, the wide range of angles corresponds to angles spaced over a range of about 180 degrees or more. In some embodiments, the limited range of angles corresponds to angles spaced over a range of about 100 degrees or less.

In some embodiments, each limited sector set of image projections is selected based on a sliding window applied to the series of time resolved image projections of the region.

In some embodiments, generating each limited sector 3D volume reconstruction based on the respective limited sector set of image projections and constrained by the time independent 3D volume reconstruction includes: generating a limited sector 3D volume reconstruction having relatively low spatial frequency components derived primarily from the respective limited sector set of projections and high frequency components derived primarily from the time independent 3D volume reconstruction.

In another aspect, a method is disclosed for producing a time-resolved three-dimensional image of a subject, the method including: acquiring image projection data from the subject using a medical imaging system during a single contrast injection, the medical imaging system including a single source/single detector system, where the acquiring includes implementing any of the methods for producing a computed tomographic image of a subject described above; generating a time-series of two-dimensional images from at least a portion of the acquired image projection data; reconstructing a three-dimensional image substantially without temporal resolution from at least a portion of the acquired image projection data; and producing a time-resolved three-dimensional image having a signal-to-noise ratio substantially higher than a signal-noise-ratio of the acquired image projection data by selectively combining the three-dimensional image substantially without temporal resolution and the time-series of two-dimensional images.

Some embodiments include producing a series of time resolved three dimensional images, where each three dimensional image in the series is generated by selectively combing the three-dimensional image substantially without temporal resolution with a respective pair of angularly displaced time resolved image projections.

In some embodiments, a subtracted vessel-only time-series of two-dimensional images is generated by subtracting at least one of a time frame of the time-series and an average of time frames of the time-series acquired before arrival of contrast from frames of the time-series acquired after an arrival of contrast during the single contrast injection.

Various embodiments may include any of the above described elements, steps, techniques, etc, either alone or in any suitable combination.

BRIEF DESCRIPTION OF THE DRAWINGS

FIG. 2 depicts an exemplary conventional CT system;

FIGS. 7A-7G provide various exemplary images associated with various method steps outlined in FIG. 6; and FIG. 8 is a flow diagram with exemplary steps using transmission information for previous projections in the same rotation, which are used to determine attenuator values.

DETAILED DESCRIPTION

Various embodiments of the present provide an implementation of CT with enhanced anatomy-selective distribution of incident radiation (e.g. an X-ray imaging beam). Traditional systems, including C-Arm CT systems, typically have excessive scattered radiation detection, which disrupts the quality of images obtained (e.g., by consuming a portion of the dynamic range of a detector). This is a major reason for the relatively low contrast/dose performance of these systems relative to conventional CT. Various embodiments of the present invention improve the resolution of C-ARM CT by performing the soft tissue component of the scan using a highly collimated modified spiral scan acquisition coupled with anatomy specific modification of the incident X-ray beam using a dynamically controlled beam attenuator for modulating the spatial intensity profile of the beam. The attenuation is determined by detected transmission information provided by the rotating detector, as detailed below.

Various methods of the present invention can be employed for collimated C-arm or conventional X-RAY CT, a small linear array of filters is driven into the X-ray beam in response to ongoing information from the detector array. The result is an improved distribution of incident radiation that provides higher signal to noise ratio in regions that would be under-penetrated in the absence of filtration. Greater contrast sensitivity is achieved in these regions due to increased local exposure. The integrated dose to the patient is often far less than in conventional CT due to the greatly reduced dose in the regions easily penetrated. The decreased radiation to the easily penetrated regions also reduces the scatter from these regions, thus further increasing the contrast/dose performance in the poorly penetrated regions.

In some embodiments, the reconstruction of CT images from the detected information includes correction of the detected data for the effects of the beam filtration. In some embodiments, this involves multiplication of the data in the attenuated regions by a filtration factor compensating for the attenuation.

Figure 1A:
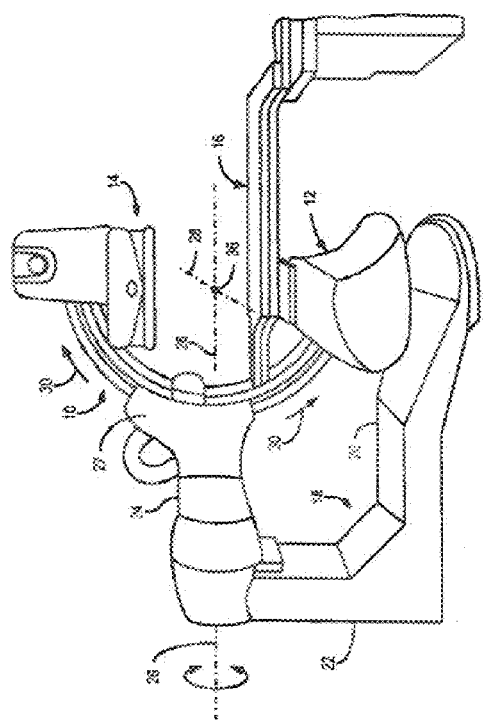
FIGS. 1A and 1B depict an exemplary rotational x-ray C-Arm CT system.

Referring to FIG. 1A, an exemplary rotational x-ray system for use in connection with interventional procedures is provided. The system is characterized by a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient.

The gantry includes an L-shaped pedestal 18 which has a horizontal leg 20 that extends beneath the table 16 and a vertical leg 22 that extends upward at the end of the horizontal leg 20 that is spaced from of the table 16. A support arm 24 is rotatably fastened to the upper end of vertical leg 22 for rotation about a horizontal pivot axis 26. The pivot axis 26 is aligned with the centerline of the table 16 and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other at an isocenter 36 located above the table 16 and they are perpendicular to each other.

The x-ray source assembly 12 is mounted to one end of the C-arm 10 and the detector array assembly 14 is mounted to its other end. The x-ray source 12 emits a beam of x-rays which are directed at the detector array 14. Both assemblies 12 and 14 extend radially inward to the pivot axis 26 such that the center ray of this beam passes through the system isocenter 36. The center ray of the beam can thus be rotated about the system isocenter around either the pivot axis 26 or the C-axis 28, or both during the acquisition of x-ray attenuation data from a subject placed on the table 16.

The x-ray source assembly 12 contains an x-ray source which emits a beam of x-rays when energized. The center ray passes through the system isocenter 36 and impinges on a two-dimensional flat panel digital detector housed in the detector assembly 14. The detector 38 is a multi- (e.g., 2048 by 2048) element two-dimensional array of detector elements, e.g., having a size of 41 cm by 41 cm (or other suitable size). Each element produces an electrical signal that represents the intensity of an impinging x-ray and hence the attenuation of the x-ray as it passes through the patient. During a scan the x-ray source assembly 12 and detector array assembly 14 are rotated about the system isocenter 36 to acquire x-ray attenuation projection data from different angles. The detector array is able to acquire a given number of projections, or views, per second and, in some embodiments, this is the limiting factor that determines how many views can be acquired for a prescribed scan path and speed. In some embodiments, the detector array is able to acquire at least about 10 scans per minute, about 20 scans per minute, about 30 scans per minute, about 50 scans per minute, or more, e.g., in the range of 10-30 scans per minute.

Figure 1B:
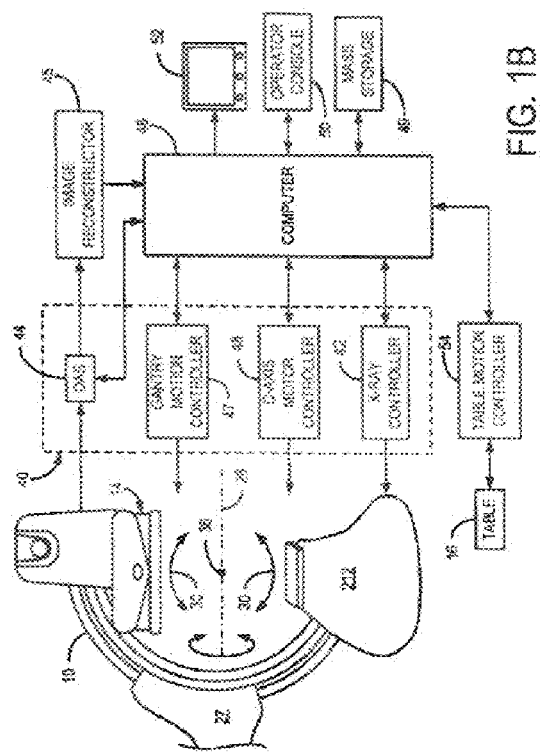

Referring particularly to FIG. 1B, the rotation of the assemblies 12 and 14 and the operation of the x-ray source are governed by a control mechanism 40 of the x-ray system. The control mechanism 40 includes an x-ray controller 42 that provides power and timing signals to the x-ray source 32. A data acquisition system (DAS) 44 in the control mechanism 40 samples data from detector elements 38 and passes the data to an image reconstructor 45. The image reconstructor 45 receives digitized x-ray data from the DAS 44 and performs high speed image reconstruction according to the methods of the present invention. The reconstructed image is applied as an input to a computer 46 which stores the image in a mass storage device 49 or processes the image further to produce parametric images according to the teachings of the present invention. It is contemplated that the computer 46 may be or include components of a digital vascular image processor (DVIP) system, e.g., of any suitable type known in the art.

The control mechanism 40 also includes gantry motor controller 47 and a C-axis motor controller 48. In response to motion commands from the computer 46 the motor controllers 47 and 48 provide power to motors in the x-ray system that produce the rotations about respective pivot axis 26 and C-axis 28. As will be discussed below, a program executed by the computer 46 generates motion commands to the motor drives 47 and 48 to move the assemblies 12 and 14 in a prescribed scan path.

The computer 46 also receives commands and scanning parameters from an operator via console 50 that has a keyboard and other manually operable controls. An associated cathode ray tube display 52 allows the operator to observe the reconstructed image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

Whereas conventional reconstruction methods generally necessitate the acquisition of a minimum number of projections dictated by the Nyquist theorem, the present invention provides a fundamentally new method for imparting temporal resolution from a time-series of 2D images into 3D image volumes to create time-resolved 3D medical images. This allows, among other things, the production of 3D angiograms with both exquisite detail and high temporal resolution. The method can be implemented using a wide-variety of medical imaging systems, such as CT systems, fluoroscopy systems, and the above-discussed rotational x-ray system, either alone or in combination. Accordingly, the present description first presents a generalized method for producing time-resolved 3D images before proceeding to more specific implementations and extensions of the method.

An exemplary conventional CT system is shown in FIG. 2. By example, the conventional CT system may include the General Electric Lightspeed system, Siemens AG Somatom system and the Phillips Brilliance system, each well known in the art.

Various methods of the present invention can be applied to C-Arm CT or conventional CT systems. In the case of conventional CT, scatter is usually reduced due to the smaller size of the discrete detector arrays. However, as more detectors are added the distinction between the two types of CT systems diminishes. In either case the use of spatially selective exposure based on detector feedback to the dynamic beam attenuator can significantly reduce dose as well as favorable alter the scatter distribution.

Figure 3:
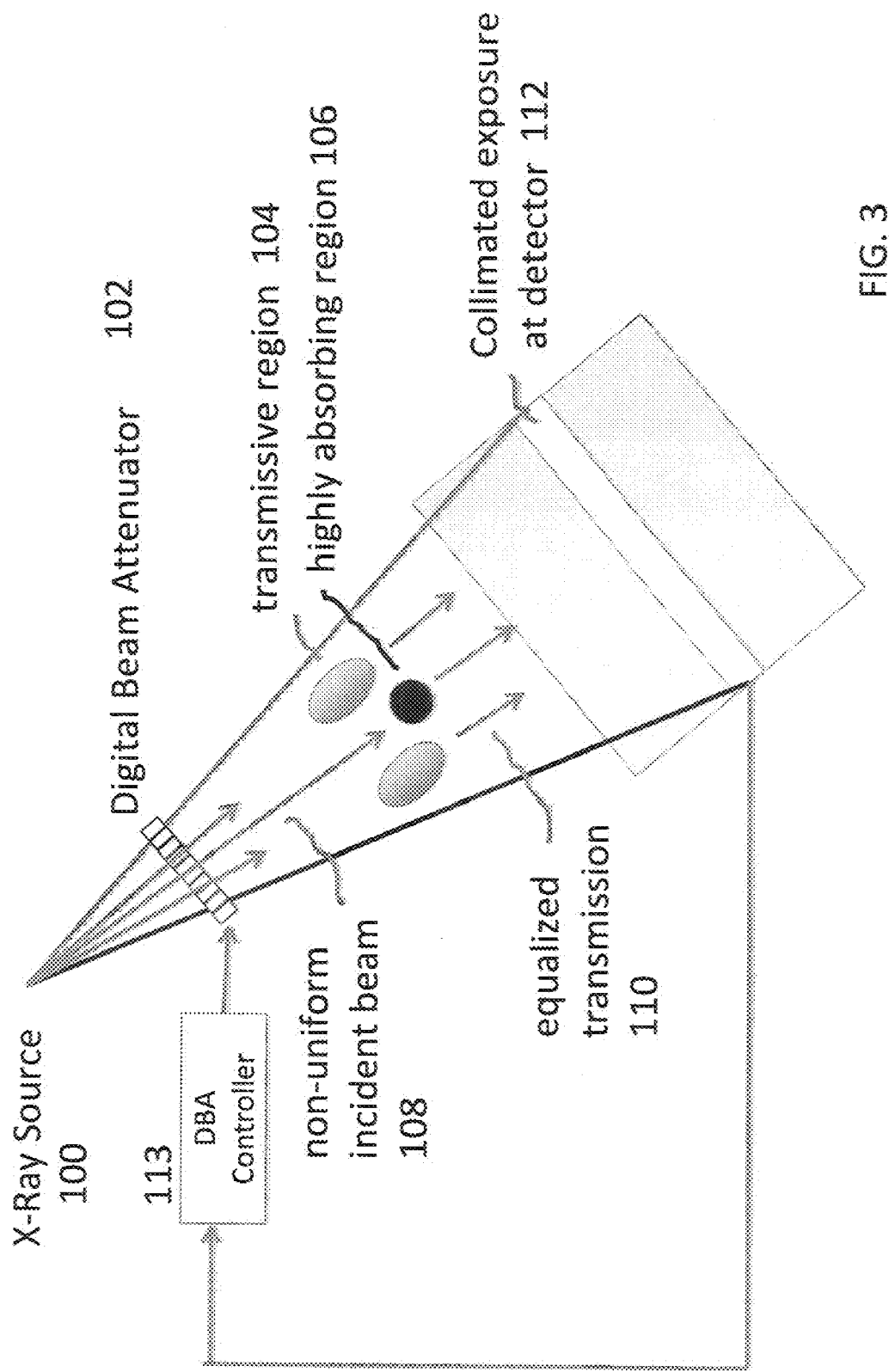
FIG. 3 is a schematic depicting a C-Arm CT system featuring beam attenuation.

FIG. 3 illustrates an imaging system featuring an X-Ray source 100 which produces a beam which is filtered in a spatially selective manner by the Digital Beam Attenuator (DBA) 102. The DBA 102 generates a spatially non-uniform beam profile resulting in equalized transmission at the detector. That is, the DBA is controlled to modulate the spatial profile of the beam such that more radiation is directed at the highly absorbing region 106 than at the highly transmissive regions 104 within the imaged region of the subject.

The amount of radiation scattered from the beam which reaches the detector 112 is reduced by collimation which exposes only a portion of the large area detector at a time. During image acquisition, the exposed portion of the detector may be scanned, e.g., by motion of one or more collimator leaves. Image information at the detector may spatially and/or angularly average, averaged to provide information to determine the attenuation to be provided by the DBA. This information is provided to the DBA controller 113 that determines the degree of filtration to be provided at each point along the DBA for each projection angle as the C-Arm rotates source 100 and detector 112.

Figure 4:
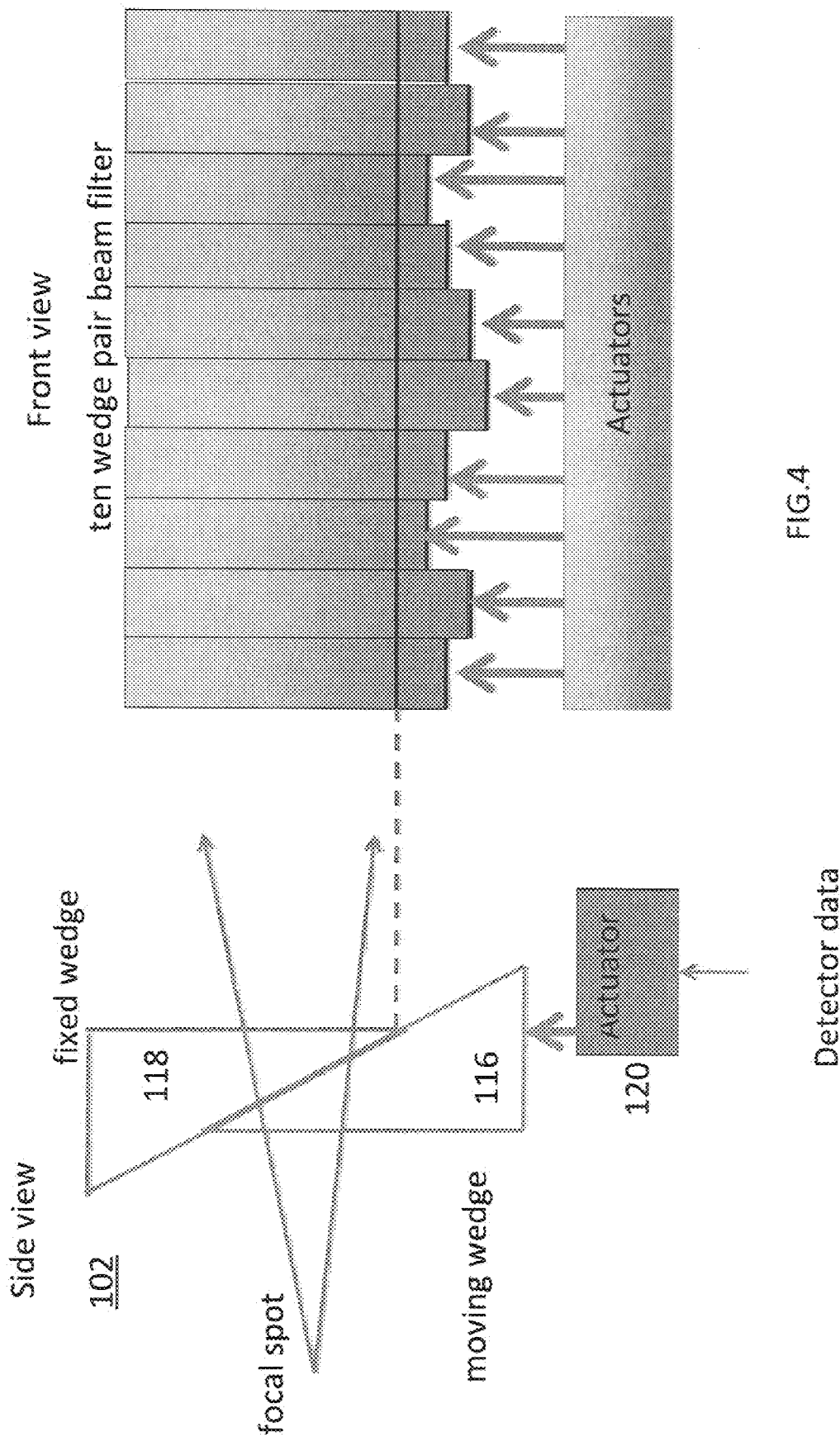
FIG. 4 is an exemplary graphical depiction of an implementation of a beam attenuator.

FIG. 4 shows an exemplary implementation of the Digital Beam Attenuator. A moving wedge 116 is paired with a fixed wedge 118 to provide adjustable attenuation. The moving wedge 116 is driven by an actuator 120 that is driven by the DBA controller 113 in FIG. 3 to adjust the attenuation of the portion of the beam incident on the wedge pair.

The DBA may include a number of wedge pairs, e.g., 2 or more, 3 or more, 5 or more, 10 or more, e.g., ten, as shown. In some embodiments there are separate actuators for each of the attenuator wedge pairs to individually control the attenuation provided by each pair.

The attenuator wedges 116, 118 can be composed of various materials, including metals and metallic alloys. For example, in one embodiment, the attenuator wedges 116, 118 are composed of copper and have a base thickness of about 10 mm. The base of each wedge 116, 118 is approximately the same width and can range from, e.g., about 0.001 mm to about 20 mm. Preferably the wedge 116, 118 thickness ranges along its length from about 10 mm to nearly 0 mm thickness. Adjacent sides of the wedges 116, 118 are contemplated to be proportional to the base as shown in FIG. 4, e.g., at a ratio of about 2 to 1, about 3 to 1, or any other suitable proportion. In an alternative embodiment the shape of the wedge 116, 118, and therefore the length and width of the wedges 116, 118 is increased or decreased based at least in part upon the proportional shape and base width. Since at least one wedge 116 moves with respect to the other wedge 118, the thickness of the x-ray filtration ranges from the base thickness of each wedge, when the wedges substantially form a rectangular element, to a thickness reaching 0.0001 mm or less, when the wedges are nearly separated. The wedges can have a base thickness greater than 20 mm and an end thickness less than 0.001 mm.

Additional suitable metals include, but are not limited to, lead and tungsten. As the attenuation coefficients differ amongst most metals the optimal wedge 116, 118 thickness will vary as well. However, considering the wedges 116 can be actuated, thicker wedges can be actuated by a greater actuation distance. In some embodiments, each wedge pair 116, 118 can present an attenuation thickness ranging from, e.g., 0 mm to greater than 20 mm. The system is capable of actuating each wedge pair 116, 118 such that one pair provides no attenuation while the other pair(s) provide a varying level of attenuation. Alternatively, the attenuation level can be the same for all wedge pairs 116, 118.

In an alternative embodiment, each wedge pair may be replaced by a set of multiple leafs (not shown) that are selectively placed completely in or out of the beam at each position. For each position there could be a family of leafs or sheets that would be selectively moved into the x-ray beam to provide a desired attenuation. The thickness of these leafs may be varied and chosen to provide a set (e.g., at each projection angle in a C-Arm sweep) that provides the desired attenuation. For example, the leafs may have attenuations differing in a binary fashion, such as leaf #1 (thickness 1 unit), leaf #2 (thickness 0.5 units), leaf #3 (thickness 0.25 units), leaf #4 (thickness 0.125), etc. For a suitable number of leafs, this may provide a near continuously selectable attenuations.

The DBA 102 can be positioned as within close proximity to the beam's focal spot (e.g., the x-ray source). In some embodiments, the position of the DBA with respect to the focal spot can be chosen based upon the size of the DBA. In one embodiment, each wedge 116, 118 can be actuated and movable with respect to the focal spot.

FIG. 4 shows an exemplary 10-wedge system. Alternatively, the number of wedges can be less than ten or greater than 10. For example a 5-wedge, 15-wedge, and 20-wedge system may be used. In various embodiments, embodiment, the number of wedges can range from about 1 to greater than 20. In another embodiment, a wedge-actuating system can utilize any suitable actuation, e.g., featuring motors and/or levering system which may feature more complicated arrangements that the 1:1 wedge actuator arrangement described above.

Figure 5:
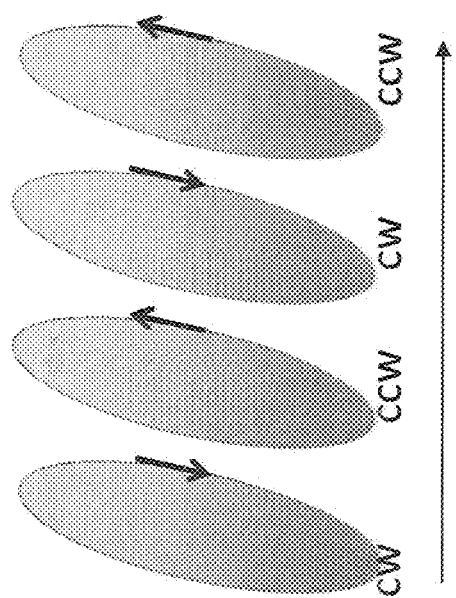
FIG. 5 depicts an exemplary modified spiral scan used for data acquisition in accordance with at least one embodiment of the present invention.

FIG. 5 shows a scanning mode in which a C-Arm is rocked back forth to produce a modified spiral scan. As shown, This can be accomplished with alternating clockwise (CW) and counterclockwise (CCW) rotational motion of the C-Arm combined while moving the imaging subject in a direction transverse to the direction of rotation, e.g., using table motion or implemented through the robot controlling the lateral position of the X-ray source and detector. For conventional CT (where 360 degree rotation of a source and detector is possible) a normal spiral scan can be implemented. For most C-arm systems where 360 degree rotation is not possible rocking back and forth between the angular extremes of the C-arm motion can be used.

For typical CT reconstruction applications, it is preferred to acquired image projections over the angular range of about 180 degrees or greater, plus the fan angle of the x-ray beam. A rocking range for various embodiments of the present invention is about 180 degrees or more, about 190 degrees or more, about 200 degrees or more, about 210 degrees or more, etc., e.g., in the range of 180-240 degrees. Depending upon the C-ARM or alternative CT system constraints the rocking range can vary. Conventional CT systems (e.g., a slip-ring equipped gantry system) may have a 360 degree range. Typical C-ARM systems feature a range less than 360, but provide sufficient angular sampling for reconstruction (e.g., using the techniques described below). Spiral scanning allows for large area scans to be accomplished in a short time even when aggressive collimation is used.

Figure 6:
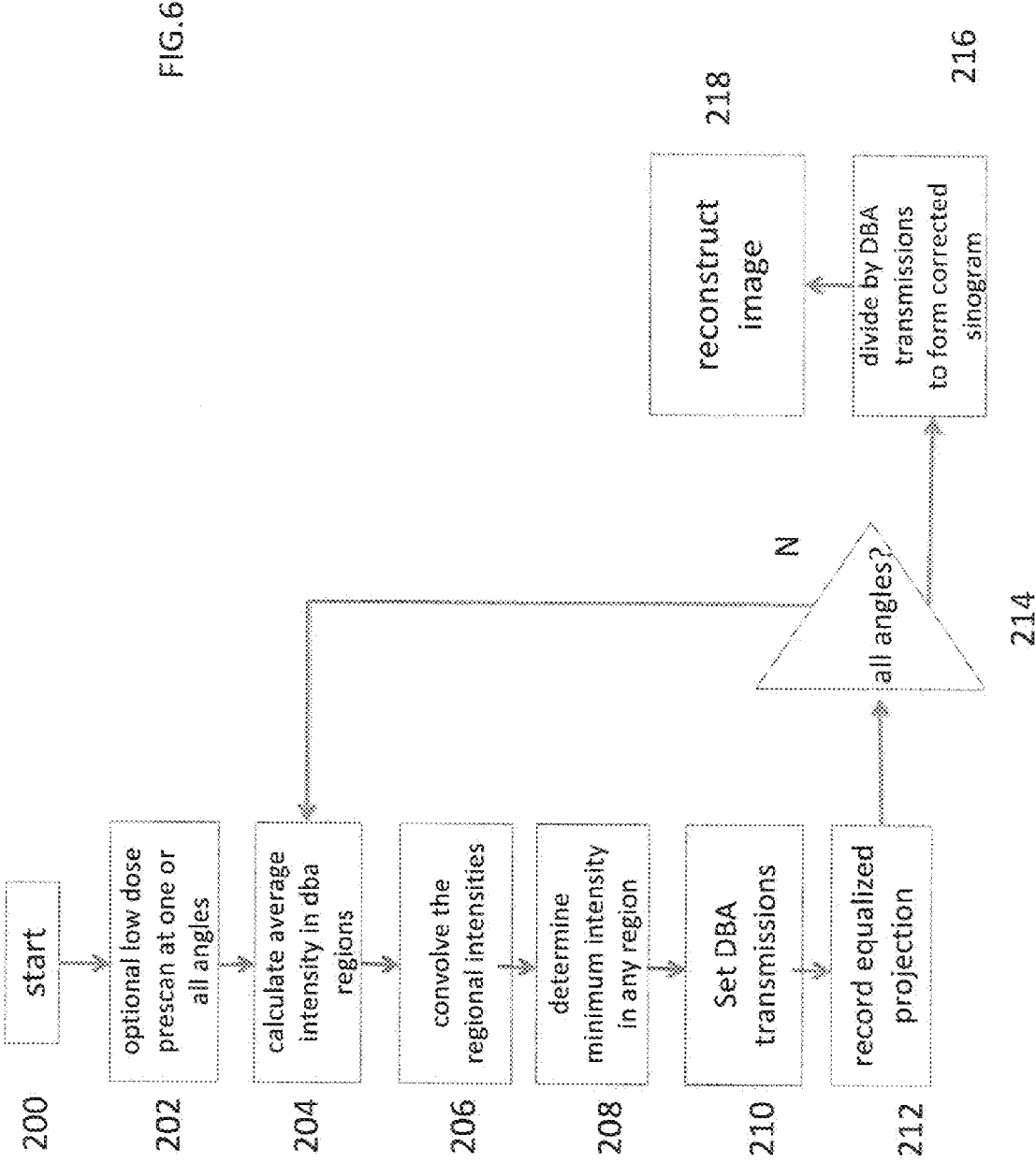
FIG. 6 illustrates the steps for implementation of the beam compensation and reconstruction algorithms in accordance with at least one embodiment of the present invention.
Figure 7A:
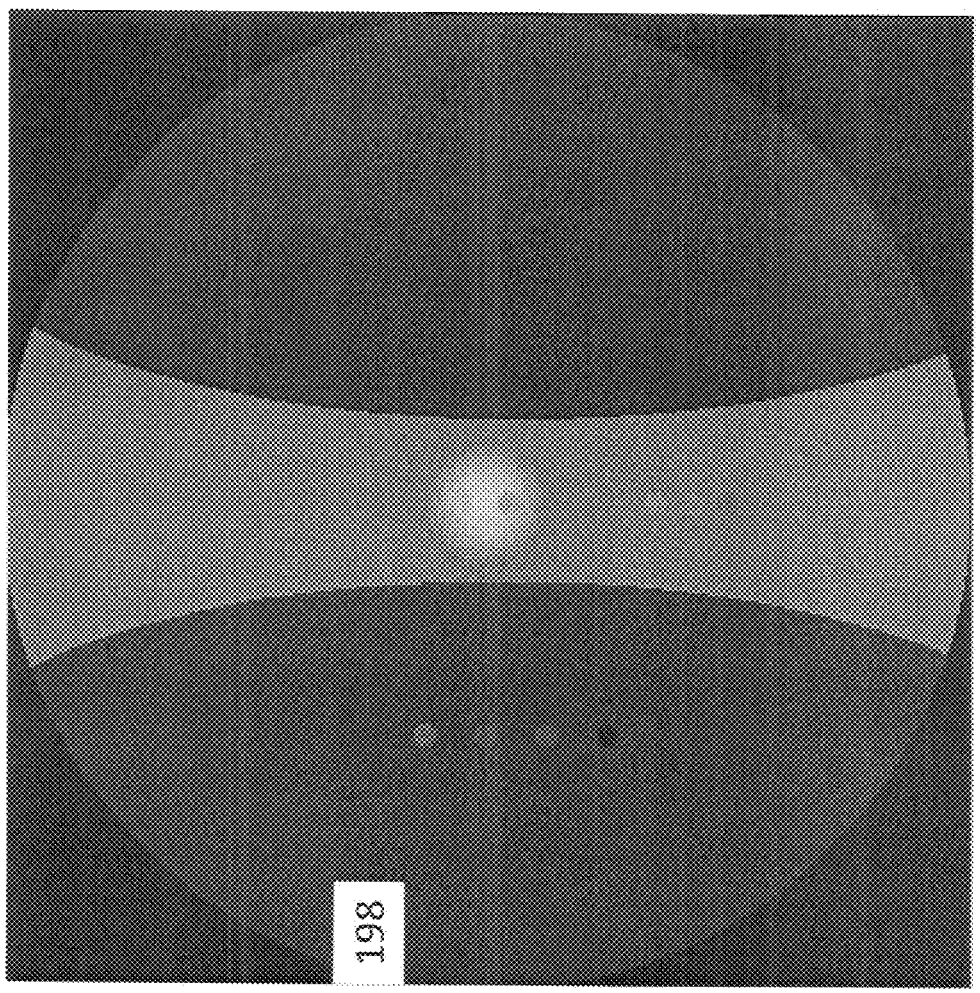
Figure 7B:
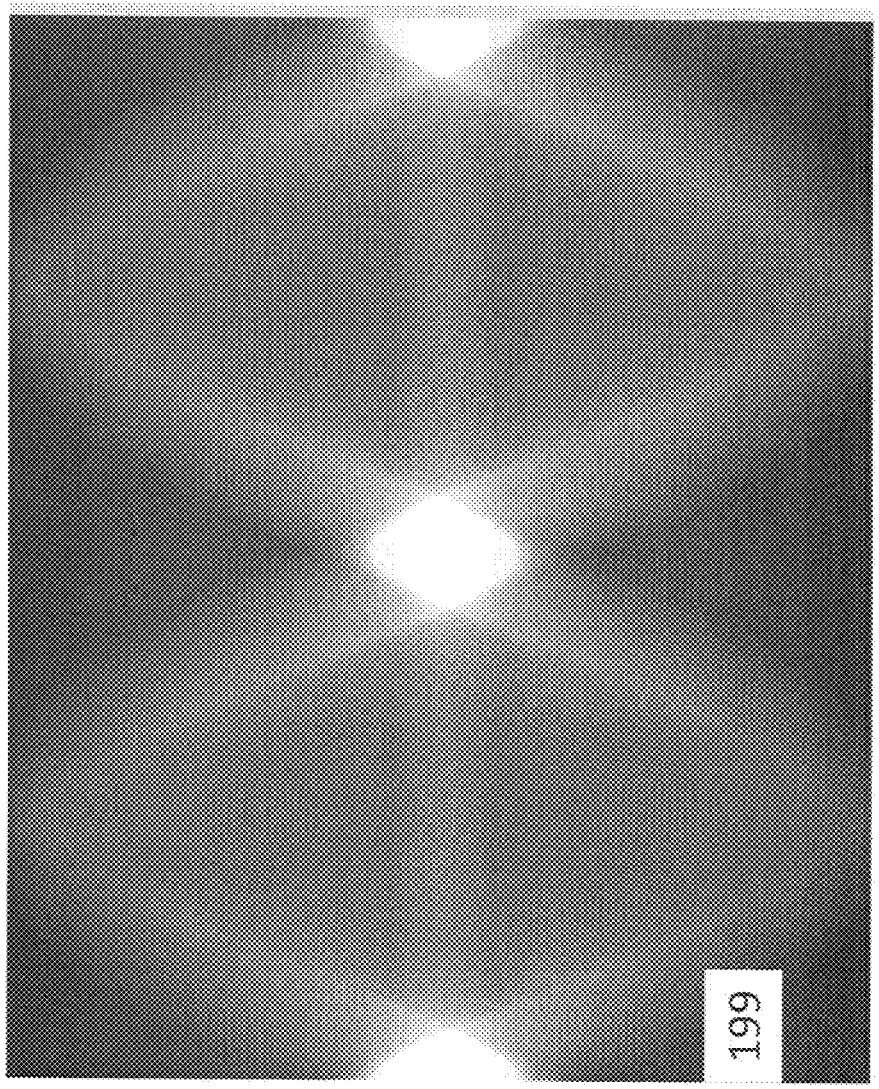

FIG. 6 illustrates the steps in a filtration reduced equalized exposure (FREE) CT process. Related images corresponding to the steps (and labeled as such) are shown in FIG. 7A—and represent the results of applying various methods of the present invention to a numerical phantom 198 shown in FIG. 7A in which regions simulating lung, bone and soft tissue have been incorporated. A sinogram 199 of the phantom is shown in FIG. 7B.

The process begins at step 200. At step 202 an optional low dose prescan is performed to determine the transmission properties of the phantom at all CT projection angles. This information may be used to establish the transmissions of the DBA wedges at all angles, e.g., to modulate the imaging beam provide a desired (e.g., uniform) intensity at the detector for each projection angle. The dose required for the prescan can be less than that used for the subsequent diagnostic scan, e.g., at least a factor of two, a factor of 5, a factor of ten, etc., less. This is because the transmission values used to establish the transmissions corresponding to a given attenuator wedge may be averaged over many adjacent pixels in each projection.

Figure 7C:
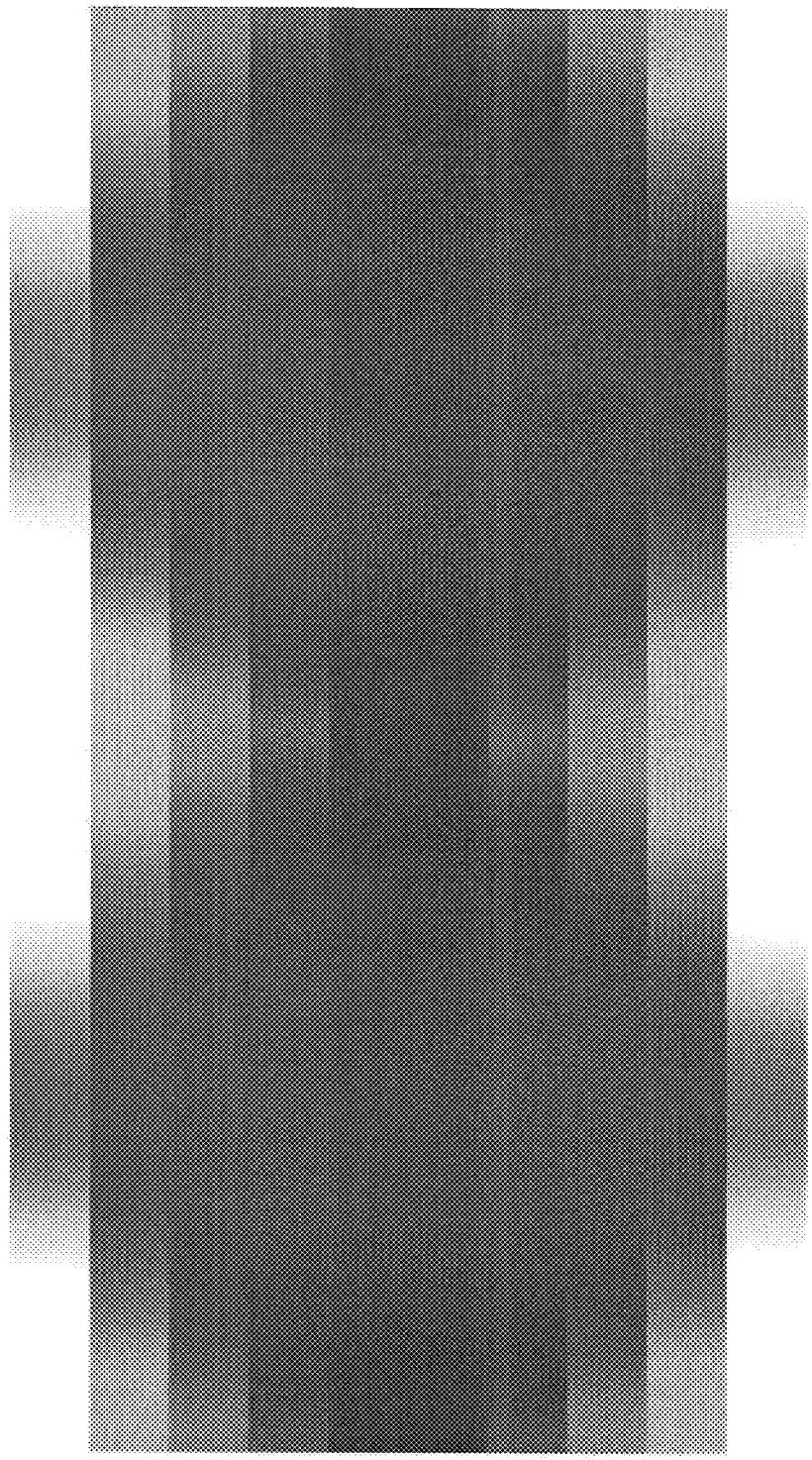

This averaging occurs in step 204. The result 204A of this for the sinogram of numerical phantom 198 is shown in FIG. 7C.

As described in detail below, in another embodiment, the initial settings of the DBA transmission elements can be set using a single projection. Subsequent attenuator settings for each projection can be determined on the basis of prior angular projections. Attenuator settings can be based upon blurred data, but dynamically modifying attenuator values during rotation may provide improved results for some applications.

Figure 7D:
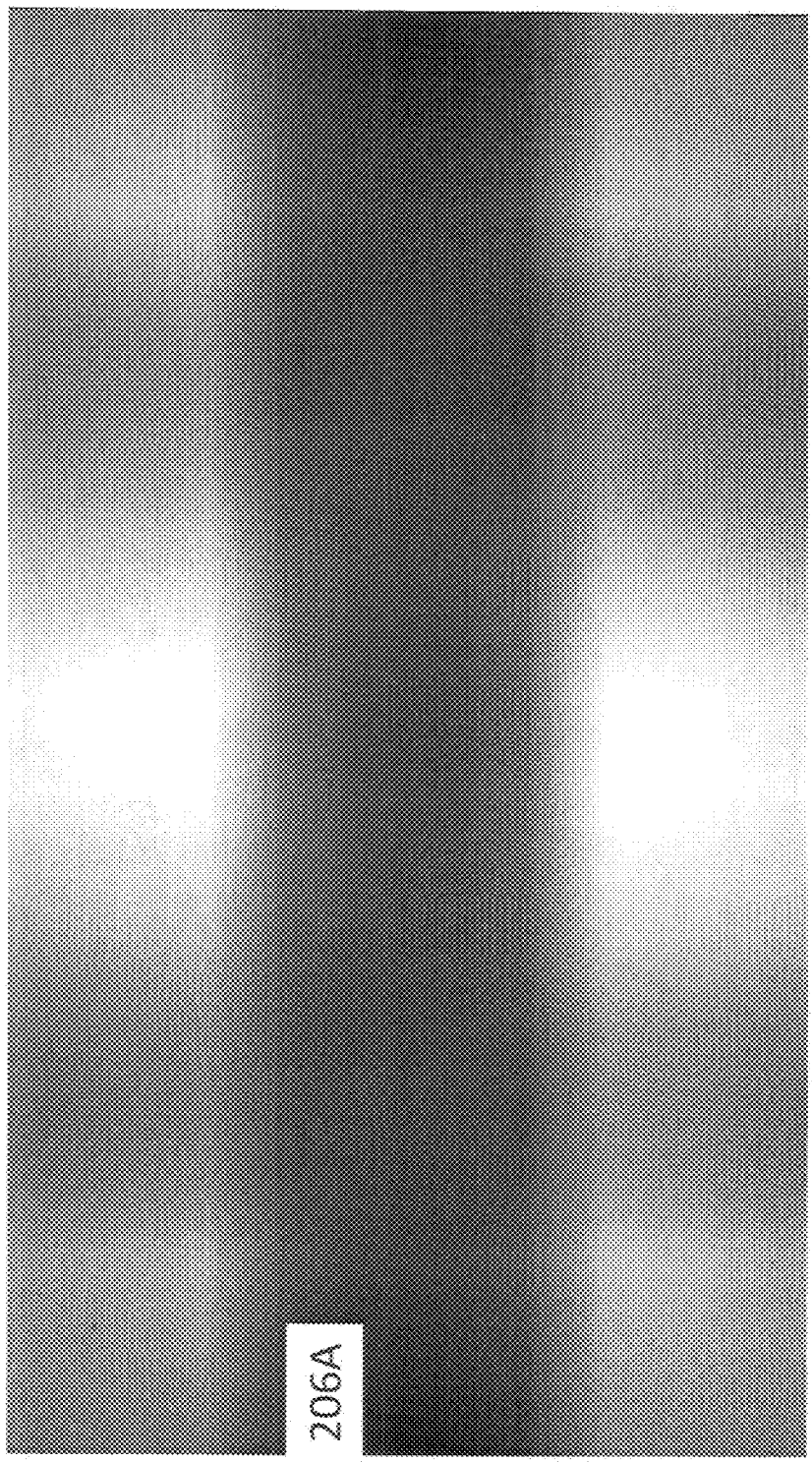

In step 206, the transmitted intensities in each DBA wedge region are convolved to smooth out extreme values that could have deleterious effects on the reconstructed image noise distribution. A convolved intensity image 206A for the phantom 198 is shown in FIG. 7D.

Figure 7E:
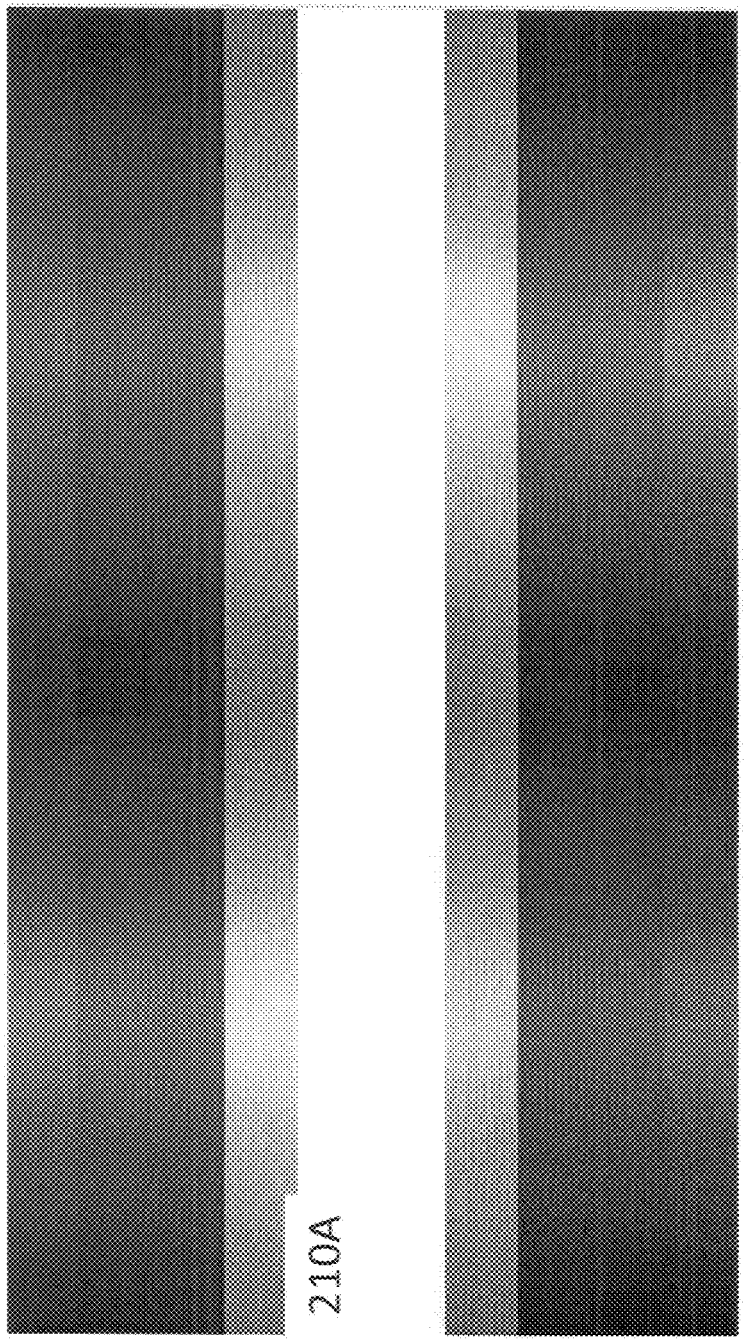

In process step 208 the minimum intensity for any wedge region is calculated for all projection angles. These are used to calculate the desired transmissions of the DBA in step 210. The desired transmissions 210A for the phantom 198 are illustrated in FIG. 7E.

In one embodiment, the DBA transmission for each wedge for each angle is determined as the ratio of the minimum transmission at each angle, divided by the observed transmissions in each wedge region at each angle so that the product of the observed transmission and the DBA transmission results in a substantially uniform transmission at each point in the projection approximately equal to the originally observed minimum transmission.

In step 212 the transmissions observed at the detector after DBA filtration are recorded at each angle until the decision block at 214 is satisfied that all angles have been acquired. Then the recorded transmissions are corrected by dividing by the DBA transmission values in step 216 to produce a corrected sinogram.

Figure 7F:
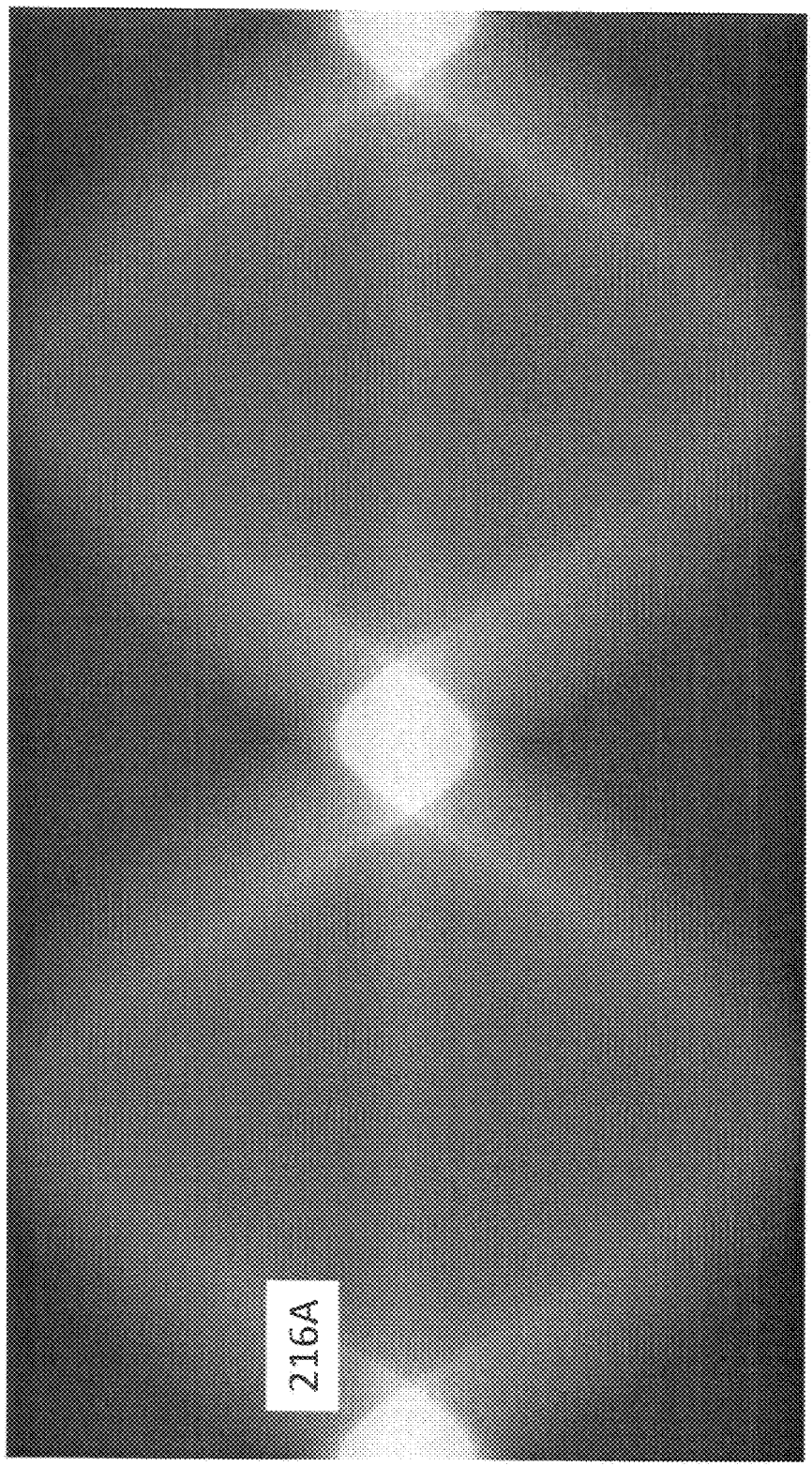

The corrected sinogram 216A for phantom 198 is shown in FIG. 7F. At step 218, for each projection angle and image is reconstructed based on the sinogram, e.g., using filtered back projection. Comparisons of reconstructed images of the phantom 198 are shown in FIG. 7G for conventional CT (left panel) and for the FREE CT process described above (right panel). Note the improved clarity and lack of artifacts in the FREE CT image. The redistribution of incident radiation has significantly improved the contrast/dose performance of the system.

A process that circumvents the need for a pre-scan to determine the DBA transmissions is shown in FIG. 8. The method is initiated at step 300, followed by obtaining a projection at an initial angle at step 302. For example, the scan can be initiated at an angle of about 150 degrees counter-clockwise from vertical and proceed for about 210 degrees in the clockwise direction. In various embodiments, other suitable initiation points and angular ranges may be used. Each projection is used to set the digital beam attenuator attenuation for the next projection at step 304. At step 306, the minimum intensity for each projection is determined. The digital beam attenuator transmissions are then set at step 308. The equalized projections are recorded at step 310. At step 312 it is determined whether all the angles are provided. If all angle projections are provided, then the projections are divided by the digital beam attenuator transmission to form a corrected sinogram at step 314. If the angle projections are not provided, then step 304 is repeated. Following the correction of the sinograms, the image is reconstructed at step 314.

When the large area detector is collimated as in FIG. 3 and used with the modified spiral scan of FIG. 5 or a step and shoot scan known in the art, a region of the detector obscured by the collimator (e.g., adjacent rectangular region parallel to the exposed region) can be used to record an estimate of scattered intensity. This information can be used for correcting the detected scatter in the exposed region. For example, the correction can be performed by subtracting the detected scatter intensity in the adjacent region from the detected intensity in the exposed region.

Using the techniques described herein, by digitally controlling the spatially variable multi-filter element, the intensity arriving at the detector can be made relatively uniform. Since the DBA equalization is of relatively low frequency, the mod-range and high spatial frequency information is recorded by the detector. The equalization process results in the x-ray beam being similarly filtered in all or most regions. This results in a reduction of well know problems associated with beam hardening artifacts.

In at least some embodiments, the dynamic beam attenuator 102 consists of a linear array of filters having, for example, a varying thickness level from about zero to about ten mm. According to at least one embodiment, the thickness of the linear array of filters is controlled by the intensity value information detected by the flat panel detector. The minimum intensity value in each projection could thereby be determined. Based at least in part upon this information and result, more or less attenuation can be added at each DBA element to force the detected intensity toward a uniform value approaching a minimum value.

Reduction of radiation in the easily penetrated regions will further reduce scattered radiation, reducing the scatter to levels below those commonly accepted in multi-detector conventional CT. For well collimated CT systems the scatter levels are often below 5%. However, as more detectors are added, the scatter fraction can significantly increase. For a large flat panel system the scatter fraction on the order of about 80% may be present. Selective exposure of regions will also greatly reduce CT dose as well as providing low contrast visibility at low dosage levels. The combination of collimated modified spiral scanning and equalization with the DBA can create scatter fractions in the flat panel systems that are substantially less. For example, the scatter fraction can be 25% or less, 10% or less, or 5% or less, e.g., in the range of 1-10%.

In general, the devices and techniques described herein may be used to generate a time resolved series of CT image projections for a region of interest in a subject. These image projections may have advantageous levels of contrast, signal to noise, etc. The image projections may advantageously be acquired while reducing or minimizing the dose to the subject.

High quality time resolved series of image projections of the type generated using the devices and methods disclosed herein may be used to generate time resolved series of three dimensional volume reconstructions of the imaged region, e.g., using techniques described in SYSTEM AND METHOD FOR FOUR DIMENSIONAL ANGIOGRAPHY AND FLUOROSCOPY, International Patent Application No. PCT/US2010/045637 and TIME RESOLVED DIGITAL SUBTRACTION ANGIOGRAPHY PERFUSION MEASUREMENT METHOD APPARATUS AND SYSTEM, U.S. Provisional Patent Application No. 61/389,086 the entire contents of each of which is incorporated by reference herein.

For example, SYSTEM AND METHOD FOR FOUR DIMENSIONAL ANGIOGRAPHY AND FLUOROSCOPY, International Patent Application No. PCT/US2010/045637 describes a method in which a time resolved series of 3D volume reconstructions is generated based on a time independent 3D volume and a time resolved series of projections. Each 3D volume in the series is generated by multiplying the time independent volume by a limited number of projections (e.g. two) from the time resolved series of projections. These techniques may provide high quality images with sufficient temporal resolution to, e.g., provide time resolved 3D digital subtraction angiography volumes using a C-Arm system. As will be understood by one skilled in the art, one or more of the time resolved series of projections used may be generated, at least in part, using the devices and techniques described herein to advantageously provide improved quality images (as is critical for certain applications, e.g., angiography of complicated vascular regions, such as the brain) and reduced subject dosing. That is, by providing high quality inputs (i.e., time resolved image projection series) to the methods described in the reference, the quality of the output of these methods (i.e., the time resolved 3D volumes) may be improved.

In typical applications (e.g., for visualizing the vasculature of a region of interest), the above described techniques provide suitable results for many DSA applications. However, in some cases (e.g., where it is desirable to image the perfusion bed of a region of interest.) it is advantageous to use the methods described in TIME RESOLVED DIGITAL SUBTRACTION ANGIOGRAPHY PERFUSION MEASUREMENT METHOD APPARATUS AND SYSTEM, U.S. Provisional Patent Application No. 61/389,086. These method provide preservation of the signals (e.g., in the tissue perfusion bed) by using a larger number of projections to generate each 3D volume in the time resolved series. In order to maintain adequate temporal resolution, the number of projections used must be less than the usual number that are used for reconstructing a time independent the 3D vascular volumes. In the case of the CT-like images acquired with a flat detector C-arm angiographic system (as described in detail below), limiting the number of projections can be accomplished by using angular sectors of projections the total temporal duration of which is limited to a clinically acceptable value, typically a fraction of a second (e.g., 1.0 seconds or less, 0.5 seconds or less, 0.25 seconds or less, etc.). For the purpose of generating artifact free, high detail images the use of angular sectors significantly smaller than 180 degrees leads to image artifacts. Accordingly, the techniques describe in this reference combine reconstruction (e.g., by filtered back projection) of these limited sectors with reconstruction constraints (e.g. based on a time independent 3D volume created using projection spanning angles of about 180 degrees or more) to reduce the impact of these artifacts on image quality.

Again, as will be understood by one skilled in the art, one or more of the time resolved series of projections used in the methods described above may be generated, at least in part, using the devices and techniques described herein to advantageously provide improved quality images (as is critical for certain applications, e.g., angiography of complicated vascular regions, such as the brain) and reduced subject dosing. That is, by providing high quality inputs (i.e., time resolved image projection series) to the methods described in the reference, the quality of the output of these methods (i.e., the time resolved 3D volumes) may be improved. For difficult imaging applications (e.g., 4D DSA perfusion measurements) this improved quality can be critically important, e.g., allowing for types of medical intervention not possible with less robust imaging techniques.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention.

For example, although in the embodiments described in detail above image projections are received directly from a C-arm system for processing, the images may be received from any other suitable source. For example, the projections may be received (e.g., in real time) from a remote source, e.g., via the internet or outer network. Accordingly, the techniques described herein may be used in telemedical and other such applications. In other embodiments, the projections may be stored, e.g. in database saved on one or more memory devices, and received for processing. Accordingly, the techniques described herein may be used in teaching, simulation, research and other such applications As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

Definitions that are contained in text incorporated by reference are excluded to the extent that they contradict definitions in this disclosure.

For the purposes of this disclosure and unless otherwise specified, "a" or "an" means "one or more."

As used herein, the term "comprising" is intended to mean that the compositions and methods include the recited elements, but not excluding others. "Consisting essentially of" when used to define compositions and methods, shall mean excluding other elements of any essential significance to the combination for that intended purpose. "Consisting of" shall mean excluding more than trace elements of other ingredients and substantial method steps for making or using the devices or articles described herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for producing a computed tomographic image of a subject comprising:
   using a radiation source and detector, obtaining radiation transmission information relating to a region of interest in the subject;
   using the source and detector; obtaining a series of projection images of the region of interest, wherein each projection image is obtained by:
      directing an imaging beam of radiation from the source through the region of interest onto the detector along a respective direction; the detector having a detection area; and
      detecting the transmission of the beam through the region of interest;
   collimating the detector by obscuring a portion of the detector area to block radiation scattered from the imaging beam; and
   while obtaining the series of projection images, filtering the imaging beam to provide a selected filtered beam intensity profile for each projection; wherein, for each projection image, the corresponding selected filtered beam intensity profile is determined based at least in part on the radiation transmission information;
   wherein the filtration applied to the imaging beam for each image projection is determined at least in part based on the detected transmission values of a respective adjacent projection in the series; and
   wherein each projection in the series is obtained within about 0.1 seconds or less of the respective adjacent projection.

2. The method of claim 1, wherein the series of projection images are obtained using a C-arm device with a movable subject table, the C-arm imaging device comprising the source and the detector; and
   further comprising:
      employing the C-Arm imaging device to obtain the series of projection images by scanning the position of the source and detector relative to the subject using at least one of table motion or motion of a C-arm of the C-arm imaging device in a direction substantially parallel to an axis of rotation of the C-Arm of the C-arm imaging device.

3. The method of claim 2, wherein the scan is a step and shoot scan.

4. The method of claim 2, wherein the scan is a modified spiral scan.

5. The method of claim 1, wherein the selected beam intensity profile for each projection image in the series is determined using unfiltered transmission information indicative of a detected transmission a corresponding unfiltered beam directed from the source to the detector.

6. The method of claim 5, wherein the series of projection images is obtained at a first dosage level; and further comprising:
   prior to obtaining the series of projection images, conducting a pre-scan with an unfiltered radiation beam at a pre-scan dosage less than the first dosage level to determine the unfiltered transmission information.

7. The method of claim 1, wherein each projection in the series is obtained within about 0.03 seconds or less of the respective adjacent projection.

8. The method of claim 1, further comprising:
   generating a sinogram based on the series of projection images; and
   correcting the sinogram based on information indicative of filtration applied to the imaging beam for each projection.

9. The method of claim 8, wherein correcting the sinogram comprises dividing each point in the sinogram by a corresponding filter transmission value.

10. The method of claim 1, further comprising constructing an image of the region of interest based on the corrected sinogram.

11. The method of claim 1, further comprising:
    determining background level information indicative of a scattered radiation background level based on radiation detected at an obscured portion of the detector area; and
    correcting at least one image projection based on the background level information.

12. The method of claim 1, wherein the source and detector are components of a C-arm imaging device.

13. The method of claim 1, wherein the source and detector are components of a conventional computed tomography imaging device.

14. The method of claim 1, further comprising:
    generating a time resolved series of images of the region of interest based at least in part on the series of projection images;
    generating a time independent three dimensional volume reconstruction of the region of interest; and
    generating a time resolved series of three dimensional volume reconstructions of the region based at least in part on the time resolved series of images and the time independent three dimensional volume reconstruction.

15. A method of providing time dependent three dimensional imaging of a region of a patient comprising blood vessels in a perfusion bed, the method comprising:
    generating a time independent 3D volume reconstruction of the region based on a series of image projections of the region acquired over a wide range of projection angles;
    generating a series of time resolved image projections of the region, at least in part, using the method of claim 1; and
    generating a time resolved series of limited sector 3D volume reconstructions of the region, wherein generating each limited sector 3D volume reconstruction in the series comprises:
       selecting a respective limited sector set of image projections from the series of time resolved image projections, the limited sector set of image projections including projections in a limited range of projection angles less than the wide range of projection angles; and
       generating the limited sector 3D volume reconstruction based on the respective limited sector set of projections and constrained by the time independent 3D volume reconstruction.

16. The method of claim 15, wherein the projections are subtracted angiography projections.

17. The method of claim 15, wherein wide range of angles corresponds to angles spaced over a range of about 180 degrees or more.

18. The method of claim 15, wherein the limited range of projection angles corresponds to angles spaced over a range of about 100 degrees or less.

19. The method of claim 15, wherein each limited sector set of image projections is selected based on a sliding window applied to the series of time resolved image projections of the region.

20. The method of claim 15, wherein generating each limited sector 3D volume reconstruction based on the respective limited sector set of image projections and constrained by the time independent 3D volume reconstruction comprises:
generating a limited sector 3D volume reconstruction having relatively low spatial frequency components derived primarily from the respective limited sector set of projections and high frequency components derived primarily from the time independent 3D volume reconstruction.

21. An apparatus for producing a computed tomographic image of a subject, the apparatus comprising:
a radiation source;
a radiation detector having a detection area;
a processor in communication with the source and the detector configured to:
obtain radiation transmission information relating to a region of interest in the subject;
obtain a series of projection images of a region of interest, wherein each projection image is obtained by
controlling the source to direct an imaging beam of radiation from a source through the region of interest onto a detector along a respective direction; and
using the detector to detect the transmission of the beam through the region of interest;
generate a time resolved series of images of the region of interest based at least in part on the series of projection images;
generate a time independent three dimensional volume reconstruction of the region of interest; and
generate a time resolved series of three dimensional volume reconstructions of the region based at least in part on the time resolved series of images and the time independent three dimensional volume reconstruction;
a collimator configured to collimate the detector by obscuring a portion of the detector area to block radiation scattered from the imaging beam; and
a dynamic beam attenuator in communication with the processor and configured to filter the imaging beam to provide a selected filtered beam intensity profile for each projection, wherein, for each projection image, the corresponding selected filtered beam intensity profile is determined based at least in part on the radiation transmission information.

22. The apparatus of claim 21, further comprising:
a C-arm imaging device with a movable subject table, the C-arm imaging device comprising the source and the detector in communication with the processor, and
wherein the processor is configured to control the C-Arm imaging device to obtain the series of projection images by scanning the position of the source and detector relative to the subject using at least one of table motion or motion of a C-arm of the C-arm imaging device in a direction substantially parallel to an axis of rotation of the C-Arm of the C-arm imaging device.

23. The apparatus of claim 21, wherein the scan is a step and shoot scan.

24. The apparatus of claim 21, wherein the scan is a modified spiral scan.

25. The apparatus of claim 21, wherein the selected beam intensity profile for each projection image in the series is determined using unfiltered transmission information indicative of a detected transmission a corresponding unfiltered beam directed from the source to the detector.

26. The apparatus of claim 21, wherein the series of projection images is obtained at a first dosage level; and wherein the processor is configured to control the source and detector to, prior to obtaining the series of projection images, conduct a pre-scan with an unfiltered radiation beam at a pre-scan dosage less than the first dosage level to determine the unfiltered transmission information.

27. The apparatus of claim 21, wherein the digital beam attenuator is configured to apply filtration to the imaging beam for each image projection at least in part based on the detected transmission values of an adjacent projection in the series.

28. The apparatus of claim 21, wherein the processor is configured to:
generate a sinogram based on the series of projection images; and
correct the sinogram based on information indicative of filtration applied to the imaging beam for each projection.

29. The apparatus of claim 28, wherein the sinogram is corrected by dividing each point in the sinogram by a corresponding filter transmission value.

30. The apparatus of claim 28, wherein the processor is configured to construct an image of the region of interest based on the corrected sinogram.

31. The apparatus of claim 21, wherein the processor is configured to:
determine background level information indicative of a scattered radiation background level based on radiation detected at an obscured portion of the detector area;
correct at least one image projection based on the background level information.

32. The apparatus of claim 21, further comprising a C-arm imaging device comprising the source and detector.

33. The apparatus of claim 21, further comprising a conventional computed tomography imaging device comprising the source and detector.

34. An apparatus for producing a computed tomographic image of a subject, the apparatus comprising:
a radiation source;
a radiation detector having a detection area;
a processor in communication with the source and the detector configured to:
obtain radiation transmission information relating to a region of interest in the subject;
obtain a series of projection images of a region of interest, wherein each projection image is obtained by
controlling the source to direct an imaging beam of radiation from a source through the region of interest onto a detector along a respective direction; and
using the detector to detect the transmission of the beam through the region of interest;
a collimator configured to collimate the detector by obscuring a portion of the detector area to block radiation scattered from the imaging beam; and
a dynamic beam attenuator in communication with the processor and configured to filter the imaging beam to provide a selected filtered beam intensity profile for each projection, wherein, for each projection image, the corresponding selected filtered beam intensity profile is determined based at least in part on the radiation transmission information;

wherein the attenuator comprises an array of filter elements controlled by the processor to provide selected filtered beam intensity profile; and wherein the processor controls the thickness of each filter element to modulate the intensity of a corresponding portion of the imaging beam.

35. The apparatus of claim 34, wherein at least one filter element comprises a pair of opposing wedge shaped members which are actuated by the processor to control the thickness of the element.

36. A method for producing a time-resolved three-dimensional image of a subject, the method comprising:

acquiring image projection data from the subject using a medical imaging system during a single contrast injection, the medical imaging system including a single source/single detector system, wherein the acquiring comprises:

using a radiation source and detector, obtaining radiation transmission information relating to a region of interest in the subject;

using the source and detector, obtaining a series of projection images of the region of interest, wherein each projection image is obtained by:

directing an imaging beam of radiation from the source through the region of interest onto the detector along a respective direction; the detector having a detection area; and detecting the transmission of the beam through the region of interest;

collimating the detector by obscuring a portion of the detector area to block radiation scattered from the imaging beam; and while obtaining the series of projection images, filtering the imaging beam to provide a selected filtered beam intensity profile for each projection; wherein, for each projection image, the corresponding selected filtered beam intensity profile is determined based at least in part on the radiation transmission information;

generating a time-series of two-dimensional images from at least a portion of the acquired image projection data;

reconstructing a three-dimensional image substantially without temporal resolution from at least a portion of the acquired image projection data; and producing a time-resolved three-dimensional image having a signal-to-noise ratio substantially higher than a signal-to-noise ratio of the acquired image projection data by selectively combining the three-dimensional image substantially without temporal resolution and the time-series of two-dimensional images.

37. The method of claim 36, further comprising:

producing a series of time resolved three dimensional images, wherein each three dimensional image in the series is generated by selectively combing the three-dimensional image substantially without temporal resolution with a respective pair of angularly displaced time resolved image projections.

38. The method of claim 37, wherein a subtracted vessel-only time-series of two-dimensional images is generated by subtracting at least one of a time frame of the time-series and an average of time frames of the time-series acquired before arrival of contrast from frames of the time-series acquired after an arrival of contrast during the single contrast injection.

* * * * *